United States Patent [19]
Horacek

[11] Patent Number: 5,175,224
[45] Date of Patent: Dec. 29, 1992

[54] POLYIMIDE FROM BIS-MALEIMIDE HAVING AZOLE RING

[75] Inventor: Heinz Horacek, Linz, Austria

[73] Assignee: Petrochemie Danubia Gesellschaft m.b.H., Schwechat-Mannsworth, Austria

[21] Appl. No.: 573,035

[22] PCT Filed: Feb. 9, 1989

[86] PCT No.: PCT/EP89/00120

§ 371 Date: Aug. 22, 1990

§ 102(e) Date: Aug. 22, 1990

[87] PCT Pub. No.: WO89/08107

PCT Pub. Date: Sep. 8, 1989

[30] Foreign Application Priority Data

Feb. 26, 1988 [AT] Austria .................. 506/88

[51] Int. Cl.⁵ .............................. C08F 22/40
[52] U.S. Cl. .................... 526/262; 524/548; 528/170; 528/321; 528/322
[58] Field of Search ........... 526/262; 528/322, 321, 528/170; 524/548

[56] References Cited

U.S. PATENT DOCUMENTS

| | | | |
|---|---|---|---|
| 3,380,964 | 4/1968 | Grundschober et al. | 260/47 |
| 3,597,426 | 8/1971 | Seltzer | 260/248 CS |
| 4,066,609 | 1/1978 | Darmony et al. | 260/42.18 |
| 4,460,783 | 7/1984 | Nishikawa et al. | 548/549 |
| 4,959,443 | 9/1990 | Yamaya et al. | 528/322 |

FOREIGN PATENT DOCUMENTS 1209460 10/1970 United Kingdom.

OTHER PUBLICATIONS

Yamaguchi et al. Chemical Abstracts 107:237486d (1987).
Koton et al. Chemical Abstracts 96:20532k (1982).
OD-009312/88 (JP 62-270623).
Hochmolekularbericht 1969:H 4121/69 (ACS Polymer Preprints 9, Feb. 1968, pp. 1143-1149).
Kwiatkowski et al., Journal of Polymer Science, vol. 13, 961-972 (1975).
Hochmolekularbericht 1987:H4082/87 (J. Polym. Sci., Polym. Chem. Ed. 13 [1975] 961-972).
Kanayama et al. Chemical Abstracts 108:132455k (1988).
Kanayama et al. Chemical Abstracts 108:6600r (1988).
Niwa et al. Chemical Abstracts 107:218275t (1987).

*Primary Examiner*—Harold D. Anderson
*Attorney, Agent, or Firm*—Wenderoth, Lind & Ponack

[57] ABSTRACT

A diamine or bismaleimide of the general formula I

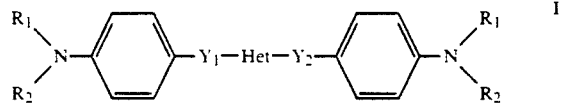

in which $R_1$ and $R_2$ denote an H atom or together denote the group $-OC-CH=CH-CO-$, $Y_1$ and $Y_2$ independently of one another deonte O or S and Het denotes a thiazole, a thiadiazole or a 1-methyltriazole ring. The diamines and bismaleimides are used for the preparation of polyimides which are if appropriate reinforced with fibers and if appropriate incompletely hardened.

6 Claims, No Drawings

POLYIMIDE FROM BIS-MALEIMIDE HAVING AZOLE RING

DESCRIPTION

The invention relates to diamines and bismaleimides, and to optionally fiber-reinforced polyimides prepared therefrom.

Polyimides based on bismaleimides are already known from U.S. Pat. No. 3,380,964, and they can be prepared by heating the bismaleimides at temperatures of 80° to 400° C., ethylene-bis-maleimide, diphenylmethane-bis-maleimide, diphenyl ether-bis-maleimide or diphenyl sulfone-bis-maleimide, inter alia, being employed.

However, an essential disadvantage of these known polyimides is that they are brittle, are difficult to melt and are sparingly soluble, so that they can be further processed only with difficulty and only to a limited degree. For example, no films or foils but only rigid laminates can be produced from them.

The object of the invention was therefore to discover diamines and bismaleimides which can be polymerized to give flexible, less brittle polyimides which can be shaped by means of heat and which can easily be further processed in subsequent operations, for example during impregnation of woven fibers or fiber mats or by compression molding.

The object was achieved with the aid of novel diamines and bismaleimides which contain a thiazole, thiadiazole or triazole ring bonded by ether or thioether groups in their chain and from which it has been possible to prepare improved polyimides.

The present invention accordingly relates to diamines and bismaleimides of the general formula I

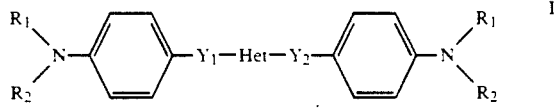

in which $R_1$ and $R_2$ denote an H atom or together denote the group —OC—CH=CH—CO—, $Y_1$ and $Y_2$ independently of one another denote O or S and Het denotes a thiazole, thiadiazole or 1-methyltriazole ring. Compounds in which $Y_1$ and $Y_2$ are identical are preferred.

In the case where $R_1$ and $R_2$ denote an H atom, the chemical compounds according to the invention are aromatic diamines, and in the case where $R_1$ and $R_2$ together denote the group —OC—CH=CH—CO—, the chemical compounds according to the invention are aromatic bismaleimides.

The substances according to the invention are prepared by reaction of dimercapto- or dihydroxy-heterocyclic compounds, preferably in the form of their alkali metal salts, of the general formula II:

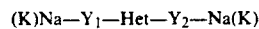

in which $Y_1$, $Y_2$ and Het have the abovementioned meaning, with chloroaniline, NaCl or KCl being split off to give the diamine according to the invention, of the general formula I. It is also possible for the compounds of the general formula II to be reacted with p-chloronitrobenzene, NaCl or KCl first being split off to give the corresponding dinitro compounds, which are then reduced by means of hydrogen to give the diamine according to the invention. The bismaleimides according to the invention, of the general formula I are obtained by reaction of the diamines according to the invention, of the general formula I, with maleic acid or derivatives thereof, for example with maleic anhydride.

The starting compounds according to the formula II are prepared by known processes, for example in accordance with DE-C-958,650 and DE-A-2,360,623, in accordance with J. V. Metzger "Thiazole and its derivatives", Chemistry of Heterocyclic Compounds, Volume 34, Part 1 (1979) page 215, J. Wiley, New York or in accordance with Frank F. Cesark (Northwestern Univ., Evanston, Ill.). Univ. Microfilms (Ann Arbor, Mich.), Order No. 61-5299, 101 pp.; Dissertation Abstr. 22,2192 (1962).

The diamines and bismaleimides according to the invention can be used for the preparation of polyimides having improved properties. The bismaleimides can be polymerized either by themselves or together with the diamines to give polyimides.

The invention furthermore relates to the polyimides prepared from the diamines and bismaleimides according to the invention. The polyimides consist of recurring monomeric units of compounds according to the formula I, the polymer bond being established via the double bonds of the maleimide radicals in the case where bismaleimides are used by themselves, and an addition of the $NH_2$ groups of the diamine onto the double bond of the maleimide radical also taking place in the case where bismaleimides and diamines are used. Polyimides which are built up from 0 to 0.8 mol of diamine per mol of bismaleimide are preferred, a molar ratio of diamine to bismaleimide of 0.2:1 to 0.6:1 being particularly preferred.

To improve the mechanical properties, the polyimides can advantageously be reinforced for certain uses with fibers, it being possible for both short fibers and fiber mats, laid fibers to be employed for the reinforcing. The content of reinforcing fibers in the composite is usually about 20–70% by weight. The weight per unit area of the fiber mats is usually about 250–1200 g/m², and that of woven fabrics about 100–300 g/m².

Glass fibers, carbon fibers, ceramic fibers or aramid fibers, or mixtures of these fibers or hybrid laid or woven fabrics can be employed, for example, depending on the requirements of the mechanical properties. Carbon fibers or aramid fibers are employed above all in instances where special requirements are imposed in particular on the strength, rigidity and low specific gravity of the components produced from the polyimides.

In many cases, it proves to be particularly advantageous for the polyimides not to be hardened completely, so that they remain still formable, fusible and thermosetting, and if appropriate can be reshaped in a subsequent hot pressing operation to give a finished component. This is of importance in the case of prepregs. Prepregs preferably consist of polyimides which are reinforced with woven or laid fibers and are only partly hardened, and they can be stored and can also be subjected to hot pressing to give the desired finished component even after some months.

The polyimides according to the invention are prepared, for example, by melting the bismaleimide according to the invention, if appropriate together with the diamine according to the invention, at temperatures of about 100° to 300° C., a temperature range of about 120° to 160° C. being particularly preferred. The starting materials are advantageously ground before and after the melting. The polyimide resin hardens more or less completely, depending on the temperature chosen and the duration of the melting. Substantial hardening of the polyimide resin can be achieved, for example, during heat treatment of about 80 minutes at about 120° C. or within about 15 minutes at about 160° C., depending on the starting substances used. If the heat treatment is not adequate, the polyimide hardens only partly, and can finally be hardened to give the desired finished component in a process step which follows at a later point in time.

To prepare fiber-reinforced polyimide resins, for example, the reinforcing fibers can be mixed with the bismaleimide and if appropriate the diamine and the mixture can then be heated and melted to form the polyimide resin. It is also possible for the fibers to be mixed with the already partly hardened polyimide powder and if appropriate for the mixture to be melted. Fiber-reinforced laminates or prepregs are prepared, for example, by impregnating a laid fibers or woven fabric with the pulverulent bismaleimide and diamine or the already partly hardened polyimide powder. Solvents, for example dimethylformamide (DMF) or N-methylpyrrolidone (NMP), can be used here, but their presence is not absolutely essential.

Continuous production of fiber-reinforced laminates is particularly advantageous, the pulverulent components, for example, being metered onto the belt of a twin-belt press and at the same time one or more layers of the fiber reinforcement being allowed to run into the press at the same time. In the twin-belt press, the mats or laid or woven fabrics are impregnated with the molten starting substances and the polyimides are formed and hardened under pressures of 1 to 20 bar and at temperatures of 100° to 300° C. Polyimide prepregs are produced, for example, on impregnating units using woven fabrics and solutions of the polyimide resin according to the invention in NMP. The concentration of the solutions is about 20–60% by weight. The temperature in the drier, for example a drying tower or a horizontal drying tunnel, is about 150°–200° C. The only partly hardened fiber-reinforced polyimide prepregs can be processed in a later processing step under the action of pressure and temperature to give a finished component, for example printed circuit boards, electrical coil cores, components of combustion engines or equipment components for aviation and space travel.

EXAMPLE 1

1.1. Preparation of the diamine
(2,5-bis-(4-aminophenylthio)thiadiazole)

The diamine was prepared in accordance with the method of E. Müller, Houben-Weyl, Methoden der Organischen Chemie (Methods of organic chemistry), volume IX (1955) page 93 and volume XI/1 (1957) page 341, G. Thieme, Stuttgart.

3 g of sodium hydroxide were dissolved in 5 ml of water in a 250 ml three-necked flask, 3.8 g (25 mmol of 2,5-dimercapto-1,3,4-thiadiazole were added and the mixture was heated to 100° C. The clear solution formed was stirred for 30 minutes, after which 79 g (50 mmol) of 1-chloro-4-nitrobenzene, dissolved in 75 ml of DMF, were added dropwise. The reaction mixture was boiled under reflux for 4 hours and then largely evaporated and the residue was cooled. The residue was taken up in water, the mixture was stirred and filtered and the residue was washed with water. The residue on the filter was dissolved in acetone and the product was precipitated with water, filtered off and dried. 8.8 g (80% of theory) of 2,5-bis-(4-nitrothiophenyl)-thiadiazole having a melting point of 210° C. and a sulfur content of 24.5% by weight was obtained.

The nitro compound was dissolved in toluene (5% strength solution), 2.5% by weight of a palladium-on-carbon catalyst (Heraeus, 5% Pd-on-C) was added and hydrogen was then passed in by means of an immersed tube at 120° C. for 7 hours until no further hydrogen was consumed. After the catalyst had been filtered off and the solution had been evaporated, 7.3 g (97% of theory) of 2,5-bis-(4-aminophenylthio)thiadiazole) were obtained.

Melting point = 253° C.
Sulfur content = 29% by weight 1.2. Preparation of the bismaleimide
(2,5-bis-(4-maleimidophenylthio)thiadiazole)

332 g (1 mol) of the diamine prepared according to 1.1 were dissolved in 500 g of DMF, and 196 g (2 mol) of maleic anhydride, dissolved in 500 g of DMF, were added in portions at −5° C. 300 g of acetic anhydride and 15 g of Na acetate (solid) were then added, the mixture was heated to 55° C. and this temperature was maintained for 1 hour. The reaction mixture was then allowed to run slowly into 5000 g of ice-water and the mixture was stirred for 3 hours, during which the bismaleimide precipitated. The precipitate was filtered off and washed with 4000 g of water until the filtrate was neutral. After drying, 454 g of 2,5-bis-(4-maleimidophenylthio)thiadiazole (90% of theory) were obtained.

Melting point = 263° C.

1.3. Preparation of the polyimide

The diamines and bismaleimides prepared according to 1.1 and 1.2 were mixed in a molar ratio of 0.4:1 and the mixture was ground to a particle size of less than 0.2 mm and melted at 150° C. in the course of 5 minutes. The resulting polyimide was cooled and ground again to a particle size of less than 0.2 mm.

24 kg/hour of the polyimide powder were metered from a pouring hopper onto the belt of a twin-belt press and at the same time a glass woven fabric having a weight per unit area of 296 g/m$^2$ (No. 92626, Interglas) was fed in. The temperature in the heating zone of the twin-belt press was 150° C., the pressing pressure was 5 bar and the belt speed was 2 m/minute. After cooling under pressure in a subsequent cooling zone of the twin-belt press, a prepreg sheet 0.23 mm thick and 1 m wide was obtained. The properties of the sheet after hardening (10 minutes at 160° C. under normal pressure, 1 hour at 180° C. under a pressure of 20 bar, 48 hours at 200° C. under normal pressure) are summarized in Table 1.

EXAMPLE 2

2.1. Preparation of the diamine
(2-(4-aminophenylthio)-4-(4-aminophenyloxo)thiazole 3 g of sodium hydroxide were dissolved in 5 ml of water in a 250 ml three-necked flask and 3.3 g (25 mmol) of rhodanine were added. The resulting clear solution was heated to 100° C. and 6.25 g (50 mmol) of p-chloroaniline, dissolved in 75 ml of DMF, were added, after which the mixture was boiled under reflux for 4 hours. It was then largely evaporated in vacuo and the residue was taken up in water. The precipitate was filtered off and dissolved in acetone and the product was precipitated with water, filtered off and dried. 6.3 g of 2-(4-aminophenylthio)-4-(4-aminophenyloxo)-thiazole (80% of theory) having a sulfur content of 20.3% by weight and a melting point of 175° C. were obtained.

2.2. Preparation of the bismaleimide (2-(4-maleimidophenylthio)-4-(4-maleimidophenyloxo)-thiazole)

315 g of the diamine prepared according to 2.1 (1 mol) were dissolved in 500 g of DMF, and 196 g (2 mol) of maleic anhydride, dissolved in 500 g of DMF, were added in portions at $-5°$ C. 300 g of acetic anhydride and 15 g of sodium acetate (solid) were then added and the reaction mixture was heated to 55° C. and kept at this temperature for 1 hour. It was then allowed to run slowly into 5000 g of ice-water and the mixture was stirred for 3 hours, during which the bismaleimide precipitated. The precipitate was filtered off and washed with about 4000 g of water until the filtrate had a pH of 7. After drying, 438 g (90% of theory) of 2-(4-maleimidophenylthio)-4-(4-maleimidophenyloxo)-thiazole of melting point 205° C. were obtained.

2.3. Preparation of the polyimide

The diamines and bismaleimides prepared according to 2.1 and 2.2 were melted together in a molar ratio of 0.4:1 at 150° C. for 5 minutes. The cooled melt was ground to a particle size of less than 0.1 mm and dissolved in NMP to give a 50% strength by weight solution (viscosity at room temperature: 0.5 Pas).

A glass woven fabric 1 m wide and having a weight per unit area of 296 g/m$^2$ (No. 92626, Interglas) was impregnated with this solution at 23° C. on a continuous impregnating unit. The gap width of the doctor blade was chosen so that a prepreg having a resin content of 40% by weight was obtained after drying at 150° C. for 8 minutes in a drying tower. The prepreg was then hardened for 15 minutes at 160° C. under normal pressure and for 1 hour at 180° C. under a pressure of 20 bar, and was conditioned for 48 hours at 200° C. under normal pressure. The thickness of the laminate was 0.24 mm and the weight per unit area was 493 g/m$^2$. The mechanical properties of the laminate are summarized in Table 1.

EXAMPLE 3

The diamines and bismaleimides prepared according to 1.1 and 1.2 were melted together in a molar ratio of 0.4:1 at 150° C. for 5 minutes. The cooled melt was ground to a particle size of less than 0.1 mm and dissolved in NMP to give a 50% strength by weight solution (viscosity at room temperature: 1 Pas). A laid fabric formed from unidirectional (UD) carbon fiber rovings (820 tex, Toho Rayon ® HTA7 12000) having 185 strands per 1 m width was impregnated with the polyimide solution on a continuous impregnating unit. The gap width of the doctor blade was chosen so that a prepreg having a resin content of 40% by weight was obtained after drying at 150° C. for 8 minutes in a drying tower. The prepreg was then hardened for 15 minutes at 160° C. under normal pressure and for 1 hour at 180° C. under a pressure of 20 bar and conditioned for 48 hours at 200° C. under normal pressure. The thickness of the laminate was 0.12 mm and the weight per unit area was 250 g/m$^2$. The mechanical properties of the laminate are sumamrized in Table 1.

EXAMPLE 4

A fiber-reinforced laminate was produced analogously to Example 3, but instead of the carbon fibers a laid fabric formed from unidirectional (UD) Kevlar 49 (aramid fiber from Du Pont) which consisted of 950 strands each of 158 tex per 1 m width was used as the fiber reinforcement for impregnation with the polyimide solution.

The hardened laminate was 0.14 mm thick and the weight per unit area was 250 g/m$^2$. The mechanical properties are summarized in Table 1.

EXAMPLE 5

A fiber-reinforced laminate was produced analogously to Example 3, but instead of the UD carbon fibers a unidirectional (UD) laid fabric formed from a ceramic fiber (Si-Ti-C-O fiber, Tyranno ® from Ube, Japan) which consisted of 1500 strands each of 100 tex per 1 m width was used as the fiber reinforcement for impregnation with the polyimide solution.

The hardened laminate was 0.12 mm thick and the weight per unit area was 250 g/m$^2$. The mechanical properties of the laminate are summarized in Table 1.

EXAMPLE 6

A fiber-reinforced laminate was produced analogously to Example 3, but instead of the carbon fibers a unidirectional glass roving from Gevetex, FRG (EC 11-2400 K 247(50)) was impregnated with the polyimide solution, as the fiber reinforcement. 65 strands each of 2400 tex were used as per 1 m width.

The hardened laminate was 1.2 mm thick and the weight per unit area was 250 g/m$^2$. The mechanical properties are summarized in Table 1.

EXAMPLE 7

7.1. Preparation of the diamine (1-methyl-3-(4-aminophenyloxo)-5-(4-aminophenylthio)-1,2,4-triazole)

3 g of NaOH were dissolved in 5 ml of water in a 250 ml three-necked flask and 2.33 g (25 mmol) of 1-methyl-3-hydroxy-5-mercapto-1,2,4-triazole (preparation according to DE-OS 2,360,623) were added. The resulting clear solution was heated to 100° C., 6.25 g (50 mmol) of p-chloroaniline, dissolved in 75 ml of DMF, were added and the mixture was boiled under reflux for 4 hours. It was then largely evaporated in vacuo and the residue was taken up in water. The precipitate was filtered off and dissolved in acetone and the product was precipitated with water, filtered off and dried, 6.33 g of 1-methyl-3-(4-aminophenyloxo)-5-(4-aminophenylthio)-1,2,4-triazole (85% of theory) being obtained. The sulfur content was 10.7% by weight and the melting point was 180° C.

7.2. Preparation of the bismaleimide 5.6 of maleic anhydride were dissolved in 28.8 ml of toluene, while stirring, and a solution of 6.9 g (23 mmol) of the diamine according to 7.1. in 15.8 ml of toluene and 4.8 ml of diemthylformamide (DMF) were metered in at a maximum of 30° C. in the course of 1 hour, a suspension of the yellow amide acid being formed. 0.45 g of p-toluenesulfonic acid was then added and the reaction mixture was boiled under reflux at 112° C. for 4 hours. During this operation, a total of 0.8 ml of water was separated off via a water separator, after which a clear solution was present.

The toluene was then distilled off in vacuo, the residue was diluted with 11.4 ml of acetone, and 28 ml of a 2% strength aqueous sodium carbonate solution was added at 10° C. in the course of 2 hours. The mixture was then stirred for 15 minutes and the precipitate formed was filtered off, washed twice with 14 ml of water and dried at 60° C. in vacuo. 9.5 g of the corresponding bismaleimide were obtained (90% of theory).

7.3. Preparation of the polyimide

The diamines and bismaleimides prepared according to 7.1 and 7.2 were sintered in a molar ratio of 0.4:1 at 150° C. for 5 minutes. The cooled melt was ground to a particle size of less than 0.1 mm and dissolved in NMP to give a 50% strength solution.

A glass fiber-reinforced laminate 0.24 mm thick and having a weight per unit area of 493 g/m² was then produced with this solution analogously to 2.3. The mechanical properties of the laminate are summarized in Table 1.

EXAMPLE 8

The diamines and bismaleimides prepared according to 7.1 and 7.2 were melted together at 150° C. in a molar ratio of 0.4:1 for 5 minutes. The cooled melt was ground to a particle size of less than 0.1 mm and dissolved in NMP to give a 50% strength by weight solution (viscosity at room temperature: 1 Pas). A laid fabric formed from unidirectional (UD) carbon fiber rovings (820 tex, Toho Rayon ® HTA7 12000) having 185 strands per 1 m width was impregnated with the polyimide solution on a continuous impregnating unit. The gap width of the doctor blade was chosen so that a prepreg having a resin content of 40% by weight was obtained after drying at 150° C. for 8 minutes in a drying tower. The prepreg was then hardened for 15 minutes at 160° C. under normal pressure and for 1 hour at 180° C. under a pressure of 20 bar, and conditioned for 48 hours at 200° C. under normal pressure. The thickness of the laminate was 0.12 mm and the weight per unit area was 250 g/m². The mechanical properties of the laminate are summarized in Table 1.

EXAMPLE 9

A fiber-reinforced laminate was produced analogously to Example 8, but instead of the carbon fiber a laid fabric formed from unidirectional (UD) Kevlar 49 (aramid fiber from Du Pont) which consisted of 950 strands each of 158 tex per 1 m width was used as the fiber reinforcement for impregnation with the polyimide solution.

The hardened laminate was 0.14 mm thick and the weight per unit area was 250 g/m². The mechanical properties are summarized in Table 1.

EXAMPLE 10

10.1. Preparation of the diamine (3,5-bis-(4-aminophenylthio)thiadizole)

3 g of NaOH were dissolved in 5 ml of water in a 250 ml three-necked flask, 3.8 g (25 mmol) of 3,5-dimercapto-1,2,4-thiadiazole (preparation analogous to U.S. Pat. No. 3,899,502 or Z. Anorgan. Allgem. Chemie volume 486 (1982), pages 111–115) were added and the mixture was heated to 100° C. 79 g (50 mmol) of 1-chloro-4-nitrobenzene, dissolved in 75 ml of DMF, were metered into the clear solution. After the mixture had been boiled under reflux for 4 hours, it was evaporated and the residue was taken up in water, washed and filtered off. After recrystallization from an acetone-water mixture, 9 g (92% of theory) of 3,5-bis-(4-nitrophenylthio)-1,2,4-thiadiazole were obtained.

The resulting nitro compound was dissolved in toluene to give a 5% strength solution, 2.5% by weight of palladium-on-carbon catalyst was added and hydrogenation was carried out at 120° C. until no further hydrogen was consumed. After the catalyst had been filtered off and the solution had been evaporated, 8 g of 3,5-bis-(4-aminophenylthio)thiadiazole having a sulfur content of 29% by weight were obtained.

10.2. Preparation of the bismaleimide 332 g (1 mol) of the diamine prepared according to 10.1. were reacted with 2 mol of maleic anhydride analogously to 1.2., 460 g of 3,5-bis-(4-maleimidophenylthio)thiadiazole having a melting point of 180° C. being obtained.

10.3. Preparation of the polyimide

The diamines and bismaleimides prepared according to 10.1. and 10.2. were dissolved in NMP in a molar ratio of 0.4:1 to give a 50% strength solution, the solution was heated to 150° C. in a tubular reactor (Ullmann, Enzyklopädie der Techn. Chemie (Encyclopedia of Industrial Chemistry), volume 3, page 350, Verlag Chemie 1973) for 5 minutes and the product was precipitated in water. The polymer which had precipitated was filtered off and the NMP was recycled. The resulting polymer was dissolved in NMP to give a 50% strength solution.

A glass fiber-reinforced laminate was then produced with this solution analogously to 2.3., the properties being summarized in Table 1.

EXAMPLE 11

The diamines and bismaleimides prepared according to 10.1. and 10.2. were dissolved in NMP in a molar ratio of 0.4:1 to give a 50% strength solution, the solution was heated to 150° C. in a tubular reactor for 5 minutes and the product was precipitated in water. The polymer which had precipitated was dissolved in NMP to give a 50% strength solution.

A laid fabric formed from unidirectional (UD) carbon fiber rovings (820 tex, Toho Rayon ® HTA7 12000) having 185 strands per 1 m width was impregnated with this polymer solution on a continuous impregnating unit. The gap width of the doctor blade was chosen so that a prepreg having a resin content of 40% by weight was obtained after drying at 150° C. for 8 minutes in a drying tower. The prepreg was then hardened for 15 minutes at 160° C. under normal pressure and for 1 hour at 180° C. under a pressure of 20 bar and conditioned for 48 hours at 200° C. under normal pressure. The thickness of the laminate was 0.12 mm and the weight per unit area was 250 g/m². The mechanical properties of the laminate are summarized in Table 1.

EXAMPLE 12

A fiber-reinforced laminate was produced analogously to Example 11, but instead of the carbon fiber a laid fabric formed from unidirectional (UD) Kevlar 49 (aramid fiber from Du Pont) which consisted of 950 strands each of 158 tex per 1 m width was used as the fiber reinforcement for impregnation with the polyimide solution.

The hardened laminate was 0.14 mm thick and the weight per unit area was 250 g/m². The mechanical properties are summarized in Table 1.

TABLE 1

| | Polyimide laminates containing 60% by weight of reinforcing fibers | | | | |
|---|---|---|---|---|---|
| | Tensile strength* (N/mm²) | Elonga- tion* (%) | Modules of elasticity* (N/mm²) | Impact strength** (J/M) | Density (g/cm³) | Reinforcement |
| 1 | 600 | 6 | 23,000 | 1000 | 2.1 | glass woven fabric |
| 2 | 650 | 5 | 24,000 | 1000 | 2.1 | glass woven fabric |
| 3 | 1700 | 1.5 | 130,000 | — | 1.7 | C fiber UD |
| 4 | 1300 | 3 | 75,000 | — | 1.4 | Aramid UD |
| 5 | 1300 | 0.8 | 90,000 | — | 2.1 | Ceramic UD |
| 6 | 1100 | 4 | 51,000 | — | 2.1 | Glass UD |
| 7 | 500 | 5 | 28,000 | 900 | 2.2 | Glass woven fabric |
| 8 | 1700 | 1.5 | 120,000 | — | 1.6 | C fiber UD |
| 9 | 1350 | 2.5 | 76,000 | — | 1.4 | Aramid UD |
| 10 | 550 | 5 | 25,000 | 1100 | 2.2 | Glass woven fabric |
| 11 | 1300 | 1.3 | 140,000 | — | 1.6 | C fiber UD |
| 12 | 1200 | 2.5 | 70,000 | — | 1.4 | Aramid UD |

*according to Standard EN 61
**according to Izod

I claim:

1. A polymaleimide of a bismaleimide having the formula I

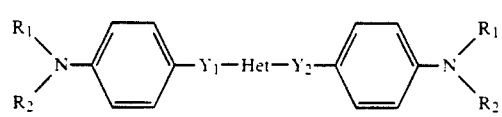

in which $R_1$ and $R_2$ together denote the group —O—C—CH=CH—CO—, $Y_1$ and $Y_2$ independently of one another denote O or S and Het denotes a thiazole, thiadiazole or 1-methyltriazole ring.

2. The polymaleimide as claimed in claim 1, wherein $Y_1$ and $Y_2$ are identical.

3. The polymaleimide as claimed in claim 1, which c is formable, fusible and thermosetting.

4. A composition comprising the polymaleimide of claim 1 and reinforcing fibers.

5. A process for the preparation of a polymaleimide as claimed in claim 1, which comprises melting the bismaleimide of the general formula I at 100° to 300° C., to form a polymaleimide resin which is incompletely or completely hardened.

6. A process for the preparation of the composition of claim 4 comprising (1) heating a mixture comprising the bismaleimide of general formula I and reinforcing fibers to a temperature of 100° to 300° C., or (2) contacting a formable, fusible, thermosetting polymaleimide of the bis maleimide of general formula I with reinforcing fibers.

* * * * *